United States Patent [19]

Weisrock

[11] 4,328,310

[45] May 4, 1982

[54] **SEMI-CONTINUOUS METHOD FOR PRODUCTION OF XANTHAN GUM USING *XANTHOMONAS CAMPESTRIS* ATCC 31601**

[75] Inventor: William P. Weisrock, Tulsa, Okla.

[73] Assignee: Standard Oil Company (Indiana), Chicago, Ill.

[21] Appl. No.: 254,696

[22] Filed: Apr. 16, 1981

Related U.S. Application Data

[63] Continuation of Ser. No. 168,969, Jul. 14, 1980, abandoned.

[51] Int. Cl.$^3$ .............................................. C12P 19/06
[52] U.S. Cl. ..................................... 435/104; 435/910
[58] Field of Search ................................ 435/104, 910

[56] References Cited

FOREIGN PATENT DOCUMENTS 1512536  6/1978  United Kingdom ................ 435/104

OTHER PUBLICATIONS

Norton et al., Society of Petroleum Engineering, (SPE Paper No. 8420, 54th AIME Meeting, 1979).

*Primary Examiner*—Lionel M. Shapiro

[57] ABSTRACT

Xanthan gum is produced by means of semi-continuous fermentation using a culture of either *Xanthomonas campestris* XCP-19 ATCC 31601 in a minimal medium, allowing the system to ferment for a period of about 24 hours, withdrawing a portion of the fermented medium, recovering xanthan from the withdrawn portion, adding fresh, sterile medium to the residual medium and repeating the above cycle.

7 Claims, No Drawings

SEMI-CONTINUOUS METHOD FOR PRODUCTION OF XANTHAN GUM USING *XANTHOMONAS CAMPESTRIS* ATCC 31601

This is a continuation of application Ser. No. 168,969 filed July 14, 1980, abandoned.

INTRODUCTION

The present invention relates to the manufacture of xanthan gum, hereinafter referred to as "xanthan". More particularly, it is concerned with an improved method for the production of xanthan by means of a semi-continuous fermentation process.

BACKGROUND OF THE INVENTION

Xanthan gum and similar heteropolysaccharides are currently manufactured by means of fermenting a suitable nutrient medium with a Xanthomonas organism, typically *Xanthomonas campestris* B-1459. The process employed involves the use of a batch method in which the inoculum medium is allowed to ferment for a period of 36-72 hours under aerobic conditions. The xanthan gum thus produced is isolated from the other components of the medium by precipitation with acetone or a low molecular weight alcohol such as methanol, in a known manner. However, because of the time required to ferment each batch, the low xanthan content of the fermented medium, and the processing required for the recovery and purification of the product, xanthan produced by batch fermentation is relatively expensive.

Insofar as I am aware, all of the installed plant capacity presently in use for the manufacture of xanthan by fermentation methods is restricted to use of the batch fermentation process. In using this particular technique, one of the chief disadvantages is the lag time required to prepare adequate quantities of inoculum (seed) for each batch run. For the quantities of nutrient medium involved in industrial operations, as much as four days time is needed to provide enough inoculum. After the fermentation has been completed and the product xanthan separated, the spent mash in the fermenter must be withdrawn and the fermenter cleaned out and sterilized before a new charge of sterile medium can be introduced.

Xanthan gum has potential application as a film forming agent, as thickeners for bodybuilding agents in edible products, cosmetic preparations, pharmaceuticals, vehicles, oilfield drilling fluids, fracturing liquids, and similar compositions and as emulsifying stabilizing and sizing agents. Xanthan also has a potential large volume use as a mobility control agent in micellar-polymer flooding. This gum possesses excellent viscosifying properties at low concentration and resistance to shear degradation and exhibits only minimal losses in viscosity as a function of temperature, pH, and ionic strength. For these reasons, xanthan is an attractive alternative to synthetic polyacrylamides for enhanced oil recovery operations.

SUMMARY OF THE INVENTION

By the present invention, the efficiency of conventional batch-type plants can be substantially improved by employing semi-continuous fermentation. This process can be effectively conducted in existing batch-type plants with a minimum of modification. In semi-continuous fermentation, the fermenter is filled to the desired volume with a suitable sterile growth medium. A culture of the desired microorganism is then introduced into the growth medium and growth and/or product formation are allowed to occur under known conditions. When the fermentation is complete, a volume of culture broth, amounting to from 25 to 90 percent of the total volume, is withdrawn and the desired culture or product is recovered. Thereafter, a volume of sterilized fresh medium is introduced into the fermenter generally equivalent to the volume recovered. The microorganisms remaining in the fermenter resume growth and/or product formation when placed in contact with the sterile medium. After fermentation is complete, the cycle is repeated. This process is usually referred to as "serial culture" or "serial transfer". The procedure is considered to be semi-continuous in that no steady-state condition is reached as in continuous fermentation but the need for fermenter cleanup and preparation of fresh culture inoculum is avoided as is required in the batch process.

However, in the production of xanthan by semi-continuous fermentation using the common strains of *Xanthomonas campestris* such as *Xanthomonas campestris* NRRL B-1459, which is generally used, are subject to degeneration after just a few serial transfers. The result of this degeneration is a loss of xanthan-producing ability and the appearance of atypical bacterial variants. This phenomenon is documented by Norton, Faulk, & Luetzelschwab (SPE Paper No. 8420, 54th AIME Meeting, 1979).

I have discovered, however, that successful production of xanthan in good yield can be obtained by the use of a novel degenerative resistant *Xanthomonas campestris* organism identified as *Xanthomonas campestris* XCP-19 ATCC 31601 and fully described in copending Application Ser. No. 168,883, filed July 14, 1980.

Subcultures of this living organism can be obtained upon request from the permanent collection of the American Type Culture Collection, 12301 Parklawn Drive, Rockville, Md. 20852. The accession number in this repository for *Xanthomonas campestris* XCP-19 is given above.

The medium employed may be an inexpensive minimal medium consisting primarily of essential inorganic salts, glucose, and $NH_4Cl$. The medium may or may not also contain a yeast extract or yeast autolysate as a supplemental nitrogen source. In general, it may be said that any nutrient medium containing essential salts and assimilable sources of carbon and nitrogen may be employed. The term "minimal medium" as used throughout the present description and claims should be interpreted to cover media of the type generally referred to herein and specifically in the example, together with modifications apparent to those skilled in the art.

The operating conditions employed in this semi-continuous fermentation process may vary widely. In general, it may be said that such conditions include the following:

| | |
|---|---|
| Agitation: | 100-2000 rpm |
| Preferably: | 500-1000 rpm |
| Air Rate: | 0.2-2.0 vol/vol/min |
| Preferably: | 0.5-1.0 vol/vol/min |
| Temperature: | 20-35° C. |
| Preferably: | 25-30° C. |
| pH: | 5-8 |
| Preferably: | 6.4-7.4 |
| Dissolved Oxygen: | 10-90% saturation |

| | |
|---|---|
| Preferably: | 20–60% saturation |

The ability of the XCP-19 ATCC 31601 strain to produce xanthan under prolonged semi-continuous fermentation conditions is illustrated in the following example which also demonstrates the inability of the well-known *Xanthomonas* organism, *Xanthomonas campestris* B-1459, to produce xanthan under semi-continuous fermentation conditions after six serial transfers without degeneration of the culture. On the other hand, XCP-19, when subjected to the same semi-continuous fermentation conditions, can undergo 10 or more serial transfers, thus forming the basis for a long-term economical fermentation process.

EXAMPLE

Inocula of *Xanthomonas campestris* B-1459 and *Xanthomonas campestris* XCP-19 ATCC 31601, were prepared by transferring a loop full of each organism from a stock culture agar slant to 7 ml of EMSY-1 broth, the composition of which is shown in Table I, followed by incubation at 28° C. and 150 rpm for 18 hours.

TABLE I

| Component | Con'n. (ppm) |
|---|---|
| Glucose | 10,000 |
| $KH_2PO_4$ | 1790 |
| $Na_2HPO_4$ | 1700 |
| Citric Acid | 500 |
| $NH_4Cl$ | 430 |
| $MgSO_4 \cdot 7H_2O$ | 424 |
| $CaCl_2 \cdot 2H_2O$ | 40 |
| NaCl | 21 |
| $FeCl_3$ | 1 as Fe |
| $ZnSO_4$ | 0.33 as Zn |
| $MnSO_4$ | 0.1 as Mn |
| $CuSO_4$ | 0.2 as Cu |
| $Na_2MoO_4$ | 0.67 as Mo |
| KI | 0.033 as I |
| $H_3BO_3$ | 0.033 as B |
| Yeast Extract | 100 |

Next, the 7 ml cultures were transferred separately to 50 ml of EMS-2 medium, the composition of which is shown in Table II, followed by incubation at 28° C. and 250 rpm for 18–20 hours.

TABLE II

| Component | Conc'n. (ppm) |
|---|---|
| Glucose | 22,500 |
| KH2PO4 | 3600 |
| $Na_2HPO_4$ | 3400 |
| Citric Acid | 500 |
| $NH_4Cl$ | 860 |
| $MgSO_4 \cdot 7H_2O$ | 424 |
| $CaCl_2 \cdot 2H_2O$ | 40 |
| NaCl | 21 |
| $FeCl_3$ | 2 as Fe |
| $ZnSO_4$ | 0.66 as Zn |
| $MnSO_4$ | 0.2 as Mn |
| $CuSO_4$ | 0.4 as Cu |
| $Na_2MoO_4$ | 0.13 as Mo |
| KI | 0.067 as I |
| $H_3BO_3$ | 0.067 as B |

To start the test, 10 ml of each culture were inoculated into 90 ml volumes of EMS-2 medium contained in 1000 ml Erlenmeyer flasks. These were incubated at 28° C. and 250 rpm for 24 hours. At this point, 10 ml volumes of the cultures were inoculated into 1000 ml flasks containing 90 ml of fresh sterile medium and incubated as before. This serial transfer process was repeated a number of times. Xanthan yield was determined on each culture broth after the 24-hour incubation period.

The results given in the Table III show that xanthan productivity by strain B-1459 starts to decline after five serial transfers, whereas strains XCP-19 continued to produce xanthan in good yields even after as many as 10 serial transfers.

TABLE III

| Transfer No. | Xanthan (gm/liter) | |
|---|---|---|
| | B-1459 | XCP-19 |
| 1 | 2.7 | 6.1 |
| 2 | 2.7 | 6.6 |
| 3 | 3.3 | 7.1 |
| 4 | 3.4 | 6.6 |
| 5 | 4.5 | 4.7 |
| 6 | 2.6 | 7.0 |
| 7 | 3.2 | 7.3 |
| 8 | 3.2 | 6.0 |
| 9 | 1.9 | 6.8 |
| 10 | 1.3 | 5.1 |

The foregoing description and Example amply demonstrate the ability of strains XCP-19 to produce xanthan by fermentation over an extended number of serial transfers, while its closely related strain, *Xanthomonas campestris* B-1459, is incapable of producing xanthan under semi-continuous fermentation conditions without degeneration.

I claim:

1. A method for the production of xanthan gum which comprises introducing a culture of *Xanthomonas campestris* XCP-19 having the identifying characteristics of ATCC 31601, into a fermentation zone containing a nutrient medium to produce both bacterial cell growth and xanthan gum, withdrawing a portion of the fermented medium from said zone, recovering xanthan gum from said portion, thereafter adding a fresh sterile volume of said medium to the residual liquid in said zone and repeating the above cycle.

2. The method of claim 1 in which the withdrawn fermented medium amounts to from about 25–90% of the total liquid volume in said zone.

3. The method of claim 1 in which said nutrient medium employed is a minimal medium.

4. The method of claim 3 in which the minimal medium contains a complex nitrogen source.

5. The method of claim 4 in which said complex nitrogen source is derived from yeast extract.

6. The method of claim 1 wherein the amount of fresh sterile medium is essentially equal to the volume of said withdrawn fermented medium.

7. In a method for the production of xanthan gum, the steps which comprise introducing a strain of *Xanthomonas campestris* bacteria identified as *Xanthomonas campestris* XCP-19 ATCC 31601, into a fermentation zone containing a liquid nutrient medium to produce both bacterial cell growth and xanthan gum, withdrawing a portion of the fermented medium from said zone, recovering xanthan from said portion and thereafter maintaining said strain in serial culture for at least 10 transfers without affecting xanthan productivity.

* * * * *